United States Patent [19]
Shikani et al.

[11] Patent Number: 5,437,656
[45] Date of Patent: * Aug. 1, 1995

[54] METHOD AND DEVICE FOR INHIBITING H.I.V. HEPATITIS B AND OTHER VIRUSES AND GERMS WHEN USING A NEEDLE, SCALPEL AND OTHER SHARP INSTRUMENT IN A MEDICAL ENVIRONMENT

[75] Inventors: Alain H. Shikani, Ruxton, Md.; Abraham J. Domb, Efrat, Israel

[73] Assignee: Leonard Bloom, Towson, Md.; a part interest

[ * ] Notice: The portion of the term of this patent subsequent to Sep. 6, 2011 has been disclaimed.

[21] Appl. No.: 92,114

[22] Filed: Jul. 14, 1993

Related U.S. Application Data

[63] Continuation-in-part of Ser. No. 998,773, Dec. 22, 1992, which is a continuation of Ser. No. 661,699, Feb. 27, 1991, abandoned.

[51] Int. Cl.⁶ .................................. A61K 9/22
[52] U.S. Cl. ................................. 604/89.1; 604/265; 623/11; 128/207.14
[58] Field of Search ............ 128/207.14, 207.15; 604/890.1, 891.1, 892.1, 96, 264, 265, 280; 623/1, 11, 12

[56] References Cited

U.S. PATENT DOCUMENTS

| | | | |
|---|---|---|---|
| 4,381,380 | 4/1983 | LeVeen et al. | 604/265 |
| 4,917,686 | 4/1990 | Bayston et al. | 604/265 |
| 4,994,047 | 2/1991 | Walker | 604/264 |
| 5,019,096 | 5/1991 | Fox, Jr. et al. | 604/265 |
| 5,019,601 | 5/1991 | Allen | 604/265 |
| 5,061,254 | 10/1991 | Karakelle | 604/265 |
| 5,102,401 | 4/1992 | Lambert | 604/264 |
| 5,165,952 | 11/1992 | Solomon | 604/265 |
| 5,344,411 | 9/1994 | Domb et al. | 604/265 |

*Primary Examiner*—C. Fred Rosenbaum
*Assistant Examiner*—Chalin Smith
*Attorney, Agent, or Firm*—Leonard Bloom

[57] ABSTRACT

An anti-infective coating for a sharp-edged metal instrument. The coating is insoluble in a biological medium and is bound to the metal instrument such as needles and scalpel blades. The coating is a biocompatible, non-hydrogel polymer. One embodiment is a coating on the metal which is complexed with an iodine solution to provide a programmed rapid release of iodine. A second embodiment is a solution of the biocompatible hydrogel polymer in which the iodine is dissolved and the solution containing iodine is coated in the sharp-edged metal instrument to provide a matrix having programmed sustained release of iodine. A coating with complexed iodine may be deposited over a coating with matrixed iodine to provide an anti-infective coating on a sharp-edged metal instrument with a rapid release and a sustained release of iodine over a period of weeks. A non-iodized polymer coating may be deposited on the complexed coating, the matrixed coating or the combined coating to provide protection to the sub coating and to further control the rate of release of iodine. The iodine containing coating provides a concentration of iodine that has sufficient activity and is available for a period of time which is long enough to allow germs to be inactivated. The coated device is stable and has long shelf life. The coated device effectively inactivates human immunodeficiency virus.

32 Claims, 8 Drawing Sheets

METHOD AND DEVICE FOR INHIBITING H.I.V. HEPATITIS B AND OTHER VIRUSES AND GERMS WHEN USING A NEEDLE, SCALPEL AND OTHER SHARP INSTRUMENT IN A MEDICAL ENVIRONMENT

CROSS-REFERENCE TO RELATED APPLICATIONS

The present application is a continuation-in-part of U.S. patent application Ser. No. 07/998,773 filed Dec. 22, 1992 pending which is a file wrapper continuation of Ser. No. 07/661,699 filed Feb. 27, 1991, now abandoned, the contents of which are hereby incorporated herein in its entirety.

FIELD OF THE INVENTION

The present invention relates to needles, scalpels and, in particular, needles used with syringes and cutting blades of scalpels that are coatable with an iodine released anti-infective, programmable polymeric dispersion and solution for inhibiting infection induced by the needles and cutting blades that penetrate a human body.

BACKGROUND OF THE INVENTION

Needles are commonly utilized especially by physicians and other health care personnel for various purposes, such as the long and short term intravenous delivery (infusion) and withdrawal of fluids, such as nutrients, blood and blood products for treatment and monitoring of the patient. Scalpels are commonly utilized by physicians and other health care personnel for opening the skin of a patient during surgical and other procedures. During use, both needles and scalpels are at least partly inserted or otherwise disposed and maintained within a patient's body.

Syringes are equipped with a needle having a cannula that are inserted directly into the vein of a patient. This is achieved by first properly aligning the needle with the target vein. Once properly aligned, the needle is pushed (directly inserted) through the patient's skin, and into their vein.

Scalpels are equipped with cutting blades having cutting portions which are inserted directly into the body of a patient. This is achieved by first properly aligning the cutting blade with that area of the patient's body in which an incision (or cut) is desired to be made. Once properly aligned, the cutting blade is pushed (directly inserted) through the patient's skin to make the desired incision.

Once a needle or a blade penetrates the skin, contact is made with the blood of the patient and droplets of blood from the patient remain on the needle or blade after their use. If this patient is a carrier of potentially infective germs in his/her blood, the infection may be transmitted to other people who accidently injure themselves with those needles or blades.

Two pathogenic germs that have been shown to be present in a potentially infective state in the blood and almost all the body fluids of infected patients are the human immunodeficiency virus (HIV) and the hepatitis B virus (HBV). Because of the logarithmic increase in the number of people that carry either of these two viruses, a serious public health problem has arisen. Although the HIV is not capable of withstanding exposure to wide ranges of temperature and humidity changes, it is stable enough in the droplets of blood to remain viable and retain infectivity for more than three days if dried and held at room temperature, and for more than a week in an aqueous environment at room temperature. HBV is even more resistant and remains viable at room temperature for 6 months. Other germs that carry similar potential infectivity include hepatitis C, D and E, different bacteria, mycobacteria and fungi. The enormous amount of used needles and scalpel blades generated by hospitals has to be disposed of in specially designed containers in order to avoid accidental injury with these sharp instruments. The problem remains acute for health care professionals, who, despite the observation of "Universal Blood and Body Fluid Precaution" developed by the Center for Disease Control in 1985, suffer an average of 2,000 needle stick injuries daily in the United States alone. A study was made by the Needle Stick Surveillance Group of the C.D.C. (Centers for Disease Control). Out of 3,978 needle sticks from patients known to be HIV positive, 13 health care workers became infected—roughly 1 out of 300. Thus, from a single needle stick while treating an AIDS patient in an operating room or other environment, the chances are roughly 1 out of 300 that the surgeon, nurse or other individual health care provider will sero-convert and become HIV positive. Also a significant public health hazard exists when needles are illegally used by intravenous drug users, get contaminated with potentially infective blood droplets and are disposed of using improper techniques.

It has been proposed to fight bacterial infection by incorporating and/or binding antibiotics and antimicrobial agents into various medical devices (such as catheters, bandages, implants, ocular inserts and interuterine devices) which are inserted into a patient's body. Once inserted, these antibiotic/antimicrobial agents are released or leeched therefrom for preventing infection. Examples of such devices are the catheters disclosed in U.S. Pat. Nos. 3,598,127 issued to Wepsic (a urinary tract catheter of nonpermeable rubber in which antibiotics, such as neomycin is infused); 4,186,745 (wherein antibacterial substances are infused into microporous polyethylene, polypropylene or polyfluorocarbon polymers); 4,054,139 issued to Crossley (wherein oligodynamic agents, such as metallic silver and other heavy metals are incorporated onto catheter surfaces); and 3,566,874 issued to Shepard (wherein antibiotics and germicides, such as penicillin and cetylpyridinium chloride are infused into a hydrophilic polymer for coating medical appliances). Other examples are disclosed in U.S. Pat. Nos. 4,603,152 issued to Lavrin; 4,642,104 issued to Sakamoto et al; 4,650,488 issued to Bays et al; 4,879,135 issued to Greco et al; 4,950,256 issued to Luthoer et al; 5,013,306 issued to Solomon et al; 5,028,597 issued to Kodama et al; 5,019,096 issued to Fox, Jr. et al; and 5,019,601 issued to Allen.

While being generally useful, in varying degrees, for their intended purposes of fighting infection on a localized level, each of these approaches suffers from one or more of the following disadvantages: (1) they merely involve mixtures and the antibacterial agent is neither chemically combined to the plastic nor slowly released; (2) the antibiotic/antimicrobial substances proposed are effective only against specific bacteria and not against aggressive microbes such as viruses (e.g., HIV and hepatitis); and (3) those disclosures involving bioerodible coatings present the undesirable side effect of also releasing the bioerodible coating into the patient's body with all of the attendant problems that that presents.

Finally, with respect to the present invention, it is noted that none of these disclosures have been directed to either needles (of syringes or otherwise) or to cutting blades (of scalpels or otherwise). Specifically, none of the above disclosures cover coating of metal surfaces.

Commonly-utilized and well-accepted for inhibiting infection is the use of iodine. Iodine is a broad spectrum antimicrobial agent that has bactericidal, fungicidal and viricidal properties. When iodine reacts with aqueous solutions, free iodine, which provides the germicidal effect, is released. While generally inhibiting infective germs over the short term, the biocidal effectiveness of iodine is dependent on, inter alia, how long the contaminant is exposed to it. This is particularly important in the case of HIV and HBV where the iodine is effective only after it remains in contact with the virus for a relatively long period of time (more than 10 minutes). Thus, over the long term, since topically applied iodine is released all at once, it does not provide adequate sustained protection. Further, such topical application is of little to no use in inhibiting internal infection either in the short term or in the long term.

To increase the effectiveness of iodine, it is normally incorporated into solutions, soaps, creams, pastes, etc., to form an iodophor. Such iodophors, in effect, provide a reservoir of iodine from which small amounts of free iodine in aqueous solution are released over a period of time. These iodophors are then topically applied to that area of a patient's body which is desired to be treated. Perhaps the best known of these iodophors is povidone-iodine, a compound of polyvinylpyrrolidone with iodine. An example of such an application can be found by reference to U.S. Pat. No. 4,010,259 issued to Johansson.

It has been disclosed to incorporate iodophors onto various medical paraphernalia for topical application. In U.S. Pat. Nos. 3,235,446 issued to Shelanski et al, iodinated polyurethane foams and films are incorporated into bandages and sponges. Similarly, U.S. Pat. No. 3,401,005 issued to Katz discloses fibrous materials (such as gauze) that are treated with combinations of polymers, halogens and iodine for use in bandages and surgical dressings. U.S. Pat. No. 4,094,967 issued to Gilbert discloses compositions method of binding iodine to polyvinylpyrrolidone with the use of cinnamic alcohol or tannic acid which is to be applied to matting, gauzes and foam rubber for topical use. U.S. Pat. No. 4,113,851 issued to Le Veen et al, discloses a composition of iodine, pyrrolidone polymer and a polymeric basic acid for incorporation into salve-ointments, dressings or bandages. U.S. Pat. No. 5,156,164 issued to Le Veen et al discloses a contraceptive sponge consisting of a polyurethane open cell foam impregnated with surfactant and iodine.

While being useful for their various purposes of generally inhibiting bacterial infection at the point of the insertion over the short term, all of those references disclose compositions into which the iodine has been complexed for topical application only. None of those references disclose compositions that are suitable for coatings for either needles or the blades of scalpels.

U.S. Pat. No. 5,071,648 issued to Rosenblatt discloses films and sponges formed from polyvinyl alcohol complexed with iodine, which provides a controlled release of iodine.

It has also been disclosed in U.S. Pat. No. 4,381,380 issued to Le Veen et al, to provide cross-linked thermoplastic polyurethane articles, such as catheters, into which iodine has been complexed for antibacterial use. While being useful for their purpose, such cross-linked thermoplastics cannot be utilized for coatings. Further, such thermoplastic polymer complexes are not readily suitable for being fabricated into either needles or cutting blades, which are in need of "razor" sharp edges.

As is well-known, polymers, such as polyurethanes, may be either essentially cross-linked or essentially uncross-linked. The uncross-linked polymers are suitable for the production of coatings, but are not of a tensile strength which is acceptable to fashion appliances, such as needles and blades, which require more exacting physical properties. The cross-linked polymers are suitable for the production of appliances, but are not suitable for the production of coatings, such as the ones noted herein. Further, cross-linked polymers possess a steric hinderance that renders inaccessible many, and sometimes all, of the linkages which complex with the iodine.

It would be extremely advantageous to provide either a surgical scalpel having a cutting blade and needles for use with syringes which has a polymer coating that has iodine that will start being released when the needle or scalpel blade come in contact with blood. The iodine is either complexed therein for quick and relative immediate release of the iodine and/or matrixed therein for sustained release of the iodine.

Thus, it can be seen that there remains a need for cutting blades and needles that are solvent coatable with a polymeric dispersion or solution that have iodine complexed and/or matrixed therein, so as to provide for immediate and/or sustained release of the iodine therefrom for inhibiting infection, that is commonly associated with the use of such cutting blades and needles.

SUMMARY OF THE INVENTION

It is the primary object of the present invention to provide a needle having a sharp edge and a scalpel having a cutting blade, each of which has thereon a surface compatible polymer coating having iodine complexed and/or matrixed therein, so as to provide for the immediate and/or sustained release of the iodine therefrom for inhibiting dissemination of germs during use thereof.

It is a still further primary object of the present invention to provide such needles and cutting blades in which the iodine release is localized and programmable, as desired.

In accordance with the teachings of the present invention, there is disclosed an anti-infective coating for a sharp-edged metal instrument used to penetrate a skin of a patient having blood or other body fluids. The anti-infective coating is insoluble in a biological medium and is bound to the sharp-edged metal instrument, during storage, use and initial disposal thereof. The anti-infective coating includes a biocompatible, non-hydrogel polymer. The polymer is compatible with and binds to a surface of the sharp-edged metal instrument. The polymer is soluble in an organic solvent. Iodine is complexed with the coating for programmed rapid release of the iodine from the coating when the sharp-edged instrument penetrates the skin of the patient and contacts blood or other body fluids.

A method is disclosed for preparing a programmed rapid release anti-infective coating for a metal instrument having a sharp edge. The coating releases iodine for a period of time at a concentration sufficient to inhibit HIV, HBA and other germs. The sharp edged metal instrument is used to penetrate the skin of a patient. The anti-infective coating is insoluble in a biological medium and is bound to the sharp-edged metal instrument. A biocompatible, non-hydrogel polymer is dissolved in an organic solvent and the solution containing the polymer is applied to the sharp-edged metal instrument. The solvent is evaporated to form a uniform polymer coating on the sharp-edged metal instrument. The coated sharp-edged metal instrument is immersed into a solution of iodine and potassium iodide in water for approximately 0.03 to 60 minutes. The iodine complexed polymer coated sharp-edged metal instrument is dried.

There is also disclosed an anti-infective coating for a sharp-edged metal instrument. Iodine is matrixed with the coating for programmed sustained release of the iodine from the coating when the sharp-edged instrument penetrates the skin of the patient.

A method is disclosed for preparing a programmed sustained release anti-infective coating for a metal instrument having a sharp-edge. The coating releases iodine for a period of time at a concentration sufficient to inhibit HIV, HBA and other germs. The sharp edged metal instrument penetrates the skin of a patient. The sharp-edged metal instrument is cleaned. A solution of a biocompatible, non-hydrogel polymer is prepared in an organic solvent. Iodine is dispersed in the solution of the polymer. The polymer/iodine solution is applied to the sharp-edged metal instrument. The solvent is evaporated to form a uniform polymer/iodine coating on the sharp-edged metal instrument. The coating releases sufficient iodine to inactivate human immunodeficiency virus.

In still further accordance with the teachings of the present invention, there is disclosed in combination with a medical device having a metallic "sharps" portion intended to pierce a human body having body fluids, a substantially biocompatible, anti-microbial, anti-viral coating on the metallic "sharps" portion. The coating is fully compatible with the normal use of the medical device and includes a non-hydrogel polymer having dispersed therein a solid solution of iodine. The iodine has a programmable timed release when exposed to body fluids, and the coating remains substantially on the device during storage, use and initial disposal thereof.

A method is disclosed for preparing a programmed release anti-infective multiple coating for a metal instrument having a sharp-edge, whereby the polymer coating is programmed to release iodine for a period of time at a concentration sufficient to inactivate HIV, HBA and other germs. The sharp-edged metal instrument is used to penetrate the skin of a patient. The anti-infective coating is insoluble in a biological medium and is bound to the sharp-edged metal instrument. The sharp-edged metal instrument is cleaned. A solution of a first biocompatible, non-hydrogel polymer in a first organic solvent is prepared. Iodine is dispensed in the solution of the polymer. The polymer/iodine solution is applied to the sharp-edged metal instrument. The first organic solvent is evaporated to form a uniform first polymer/iodine coating on the sharp-edged metal instrument. A second biocompatible, non-hydrogel polymer is dissolved in a second organic solvent to form a second solution. The second solution containing the polymer is applied to the first polymer/iodine coating on the sharp-edged metal instrument. The second solvent is evaporated to form a second uniform polymer coating on the sharp-edged metal instrument. The coated sharp-edged metal instrument is immersed into a solution of iodine and potassium iodide in water for approximately 0.03 to 60 minutes. The iodine complexed polymer coated sharp-edged metal instrument is dried. The outer coating provides short term programmable timed release of iodine and the inner coating provides long term programmable release of iodine.

These and further objects and advantages of the present invention will become readily apparent from a reading of the following description and examples, taken in conjunction with the enclosed drawings.

DESCRIPTION OF THE PREFERRED EMBODIMENTS

Figure 1:
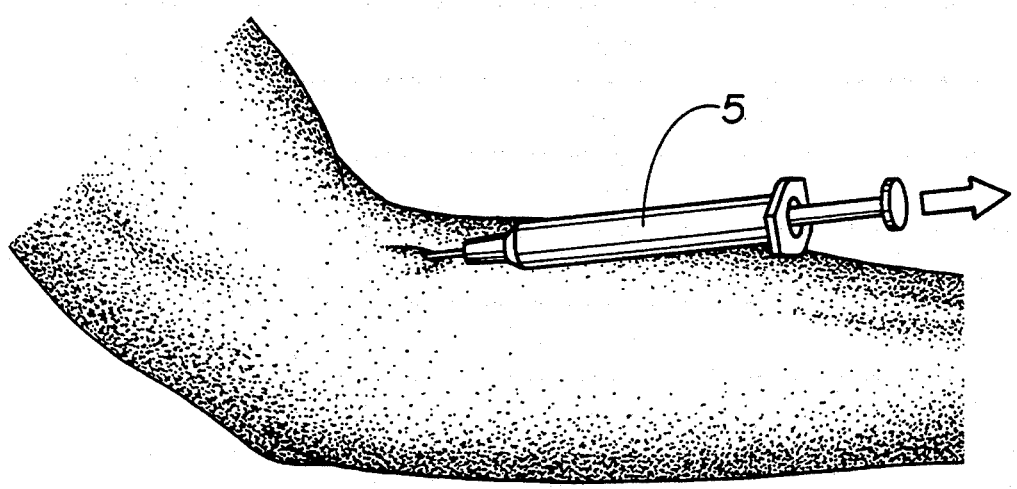
FIG. 1 illustrates the use of a needle with a syringe in its environment to withdraw fluids from the vein of a patient for the treatment and/or monitoring thereof and to infuse fluids, such as nutrients, antibiotics and the like into the vein.
Figure 2:
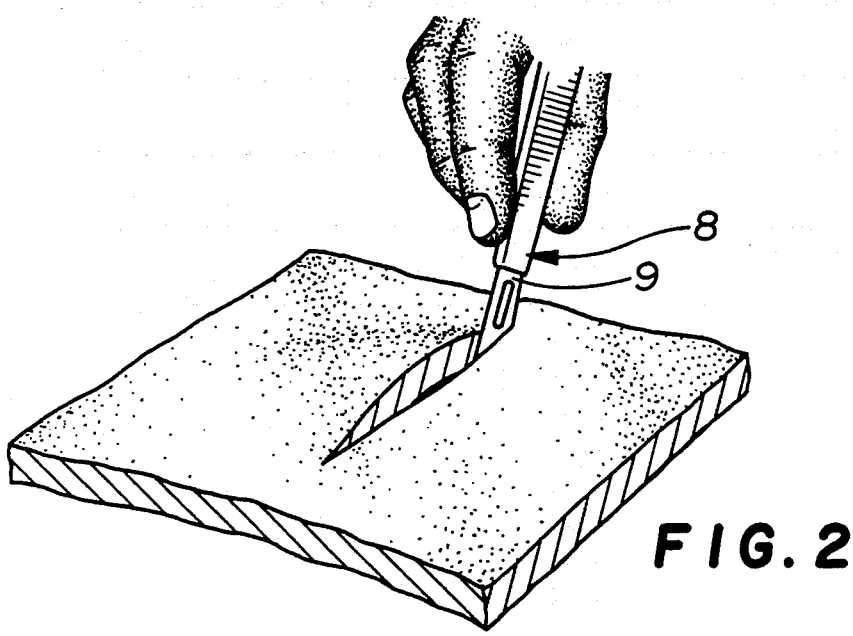
FIG. 2 illustrates the use of a scalpel in its environment to cut open a patient's skin during a surgical procedure.

Referring now to FIGS. 1-2, a needle 5 having a cannula 6 with a sharp edge is inserted directly through the skin of a patient into a vein. The needle 5 may be connected to a syringe to introduce medication into the patient or to withdraw body fluids. The needle 5 also may be connected to a container holding fluid to be infused into the patient.

A scalpel 8 has a cutting blade 9 with a sharp edge 10. the sharp edge 10 is used to cut the skin of the patient.

A potentially serious problem arises due to the opening in the patient's skin which permits the presence of blood droplets on the surface of needles and blades (commonly called "sharps") which could infect the individuals who accidentally cut themselves with the contaminated needles and blades.

Referring now to FIGS. 3A and 3B through 5A and 5B, the needles 5 having sharp edges, and the scalpels 8 having the cutting blades 9 of the present invention are discussed.

The needles 5 and scalpels 8 of the present invention, are standard needles and scalpels which have biocompatible, non-hydrogel polymer coating(s) 12, 13 and 14 thereon. Commonly, these needles 5 and scalpels 8 are fabricated from metals, such as stainless steel, aluminum and carbon steel electroplated with nickel.

In order to avoid the problems of infection discussed above, the polymer coating(s) 12 and 13 have elemental iodine matrixed and/or complexed therein. Water in the fluids that are naturally present in the patient's body contact the iodine, dissolving the iodine from the coating(s) 12 and 13. In this manner, a programmable sustained and/or (controlled) immediate release of the iodine from the coating(s) 12 and 13 respectively, is provided.

It is noted that the polymer-iodine coatings 12 and 13 on the needles 5 and cutting blades 9 of the present invention provide localized delivery of iodine at relatively high concentrations in the immediate area which is critically affected. The released iodine is then available to kill and/or otherwise inhibit the microbe, including bacteria and viruses, that can result in infection. Finally, the release of the iodine from the coatings 13 and 12 is programmable, so that it may occur either immediately or in a controlled, sustained manner over a prolonged period of time ranging from a few minutes to several weeks or longer.

Pursuant to the teachings of the present invention, the polymers used in the coatings 12, 13 and 14 of the present invention exhibit the following traits: (1) the polymers are soluble or dispersible in solution in order to be disposed onto the surface of the needles 5 and cutting blades 9 (in this regard, it is noted that thermoplastic and cross-linked polymers that are insoluble are not useful); (2) the polymers do not chemically react with iodine; (3) the polymers are compatible with iodine, so as to form a uniform, solid complex or matrix with the iodine; (4) the polymers are capable of adhering to the surface of the needle 5 and cutting blade 9; (5) the polymers are capable of forming a uniform coating on the surface of the needle 5 and cutting blade 9; and (6) the polymers are capable of forming polymer-iodine complexes and matrixes which remain stable during storage, so as to avoid a significant loss of iodine therefrom.

All of these polymers are biocompatible, so as to not cause or result in adverse reactions in the patient's body. Furthermore, all of these polymers are nonbioerodible, so that they are not inadvertently released into the patient's body. The polymers are insoluble in water and/or body fluids and remain bound to the metal surface even after the iodine in the respective coatings has been released. The polymers of the present invention are non-hydrogel insofar as the polymers swell only slightly when in contact with water. This is distinguished from polymers such as polyvinylalcohol which, after exposure to water, may swell up to 100% of the volume prior to exposure to water. This consideration is one factor which permits multiple coatings of the present invention as will be described. A polymer which swells cannot be used as a base for another polymer to be coated over the base coating. The polymers preferably have a molecular weight of more than 1,000.

In this manner, the polymers of the present invention are distinguishable from previous coatings such as the polyvinylalcohol coating of Rosenblatt (U.S. Pat. Nos. 4,381,380 and 5,156,164) which is not soluble or dispersible.

The polymers utilized in the iodine complexed coating 13 is preferably polyurethane or polyurea. The polymers utilized in the iodine matrixed coating 12" is selected from the group consisting of polyurethane, ethylene vinyl acetate, polyvinylchloride, polyesters, nylon, polyacrylamide, polycarbonate, polyethylene, polymethyl methacrylate, cellulose esters (like ethyl, methyl, propyl and hydroxypropyl) propylene, polystyrene, polyterefluoroethylene, polyvinylchloride, poly(ethylvinyl acetate), elastomeric organosilicon polymers, poly(hydroxy alkyl esters), copolymers and combinations thereof.

Preferably, the coatings 12, 13 and 14 are between 0.01 and 1.0 mm in thickness and, most preferably, between 0.1 and 0.22 mm in thickness.

The polymer coatings may be formed by solvent casting or melting. The polymer coatings 12, 13 and/or 14 are applied to the surfaces of the needles 5 and cutting blades by dipping, spraying, brush coating, or any other suitable method.

The iodine utilized herein is elemental iodine. As shall be discussed at greater length below, the iodine may be incorporated into the polymer coatings 12 and 13 either by matrixing at the time of manufacture (casting or melting), or subsequently thereto, by complexing such as by absorption therein to obtain a solid solution of the iodine. The solid solution is a mixture or distribution of iodine molecules within the polymer chains. This solid solution is differentiated from a physical mixture of iodine particles dispersed in the polymer.

In the needles 5 and cutting blades 9 of the present invention, the polymer/iodine complexes 12' 13 are formed by complexing the iodine with the polymer coating after the polymer coating has been applied to the surface of the needles 5 and cutting blades 9. This can be achieved by spraying, dipping or painting an iodine solution on the needles 5 and the cutting blades 9 that already have the polymer coating thereon. Iodine release occurs by decomplexation or desorption of the iodine as a result of an equilibrium between the polymer coating 12', 13 and the surrounding medium. Since iodine in a polymer-iodine complex may be easily contacted and dissolved by the water in the body's natural fluid, the release of complexed iodine from the iodine-polymeric coatings 12', 13 of the present invention occurs relatively fast and, generally-speaking, immediately. Iodine can be complexed and loaded by immersing the polymer-coated needles 5 and cutting blades 9 in an iodine solution in water or alcohol. The kind of polymers that are capable of complexing iodine are those that contain urethane or urea bonds.

In the needles 5 and cutting blades 9 of the present invention, the polymer/iodine matrixes are formed by dissolving solid elemental iodine into the polymer solution to form the polymer-iodine matrix. The polymer-iodine matrix is then subsequently formed onto a surface of the needles 5 and cutting blades 9 by spraying, dipping or painting the surface with the polymer-iodine matrix solution. The iodine is released from the polymer matrix by diffusion as a result of water penetrating into the matrix, dissolving the iodine and carrying it out into the surrounding medium. Since, it is more difficult (as compared to complexed iodine) for matrixed iodine to be contacted and dissolved by the water in the body's natural fluids, the release of matrixed iodine from the polymeric coating 12" is more sustained than is the release of complexed iodine from the polymeric coating 12', 13

Figure 3A:
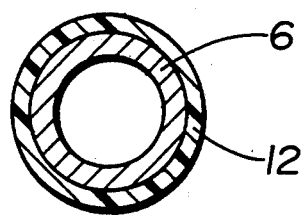
FIGS. 3A and 3B are cross-section views of first embodiments of, respectively, the needle and the scalpel having the cutting blade of the present invention wherein iodine is complexed/matrixed into a polymer coating on the needle and the cutting blade for the release of the iodine from the coating to inhibit infection.
Figure 3B:
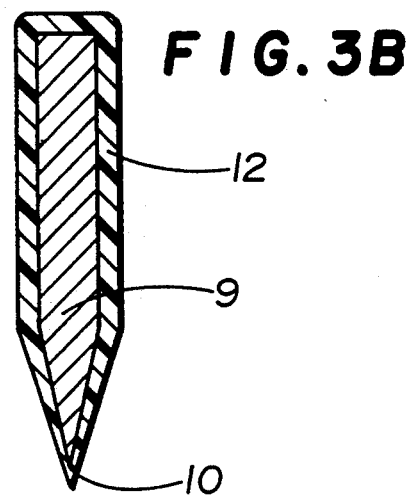

With particular reference now to FIGS. 3A and 3B, the first preferred embodiments of, respectively, the needles 5 and the cutting blades 9 of the scalpels 8 of the present invention are illustrated. In these first embodiments, a polymer coating 12' is directly disposed on the surfaces of the needles 5 (exterior and interior surfaces) and the cutting blades 9. The polymeric coating 12' has iodine complexed therein. Complexing of the iodine in the polymeric coating 12' means that the iodine may be easily contacted and dissolved by the water in the body's natural fluid for quickly immediately releasing the iodine from the polymeric coating 12'.

The second preferred embodiments of, respectively, the needles 5 and the cutting blades 9 of the scalpels 8 of the present invention are illustrated (FIGS. 3A and 3B). In these second embodiments, a polymer coating 12" is directly disposed on the surfaces of the needles 9 (exterior and interior surfaces) and the cutting blades 9. The polymeric coating 12" has iodine matrixed therein. As will be readily understood by those skilled in the art, matrixing (as opposed to complexing) of the iodine makes contact of the iodine with water in the body's natural fluids (contact that would dissolve the iodine) more difficult. In this manner, the release of the iodine from a polymer coating 12" in which it is matrixed, is slower than that of complexed iodine, so that the matrixed iodine release is sustained and controlled.

In FIGS. 3A and 3B, the coatings are enlarged and are not to scale to more clearly show the structure. The inner coating 12 has not been designated as either a complex coating 12' or a matrix coating 12" but either may be used as desired.

Figure 4A:
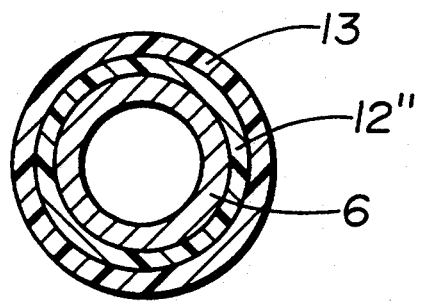
FIGS. 4A and 4B are cross-section views of third embodiments of, respectively, the needle and the scalpel having the cutting blade of the present invention wherein iodine is matrixed into a biocompatible, non-hydrogel polymer inner coating on the needle and the cutting blade for the programmable (controlled) sustained release of iodine from the inner coating, and further wherein iodine is complexed into a biocompatible, non-hydrogel polymer outer coating on the needle and the cutting blade for the programmable immediate release of iodine from the outer coating to inhibit infection.
Figure 4B:
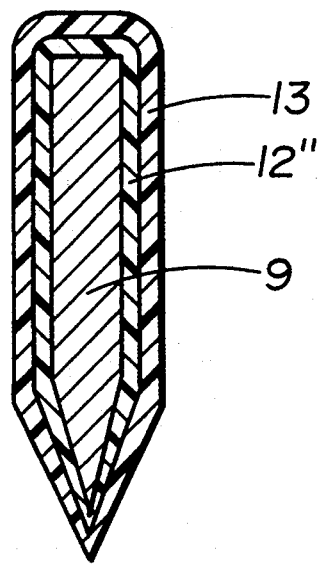

With particular reference now to FIGS. 4A and 4B, the third preferred embodiments of, respectively, the needles 5 and the cutting blades 9 of the scalpels 8 of the present invention are illustrated. In these third embodiments, a first, inner polymer coating 12" is directly disposed on the surfaces of the needles 5 (interior and exterior) and the cutting blades 9. The inner polymeric coating 12" has iodine matrixed therein. A second, outer coating 13 is disposed on the inner coating 12". The outer polymeric coating 13 has iodine complexed therein. In this fashion, such a two-layer polymeric coating provides both an immediate release (from the complexed coating) as well as a continuous and sustained release (from the matrixed coating) of iodine therefrom. The coatings are enlarged and are not to scale to more clearly show the structure.

In this regard, it is noted that the presence of the outer coating 13 acts to further shield the iodine in the polymer-iodine matrix of the inner coating 12" from the water in the body's natural fluids. In this fashion, the release of the matrixed iodine from the inner coating 12" may be programmed, so as to be further slowed. This feature provides an even greater sustained release of the iodine therefrom than is available from the single polymer-iodine matrix coating 12" of FIGS. 3A and 3B. In this manner, infection of the human body about the needles 5 and the cutting blades 9 of the present invention is inhibited over a longer period of time.

Figure 5A:
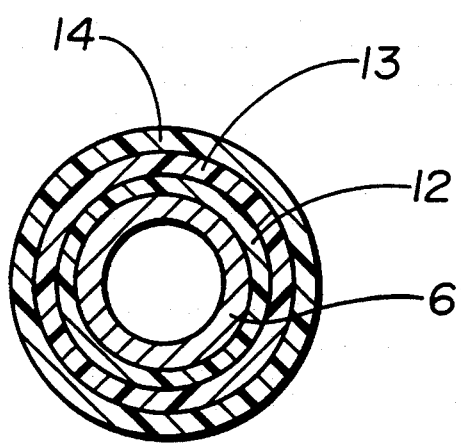
FIGS. 5A and 5B are cross section views of another embodiment of respectively, the needle and the scalpel, wherein inner coating and outer coating of FIGS. 4A and 4B further are coated with a polymer having no iodine therein.
Figure 5B:
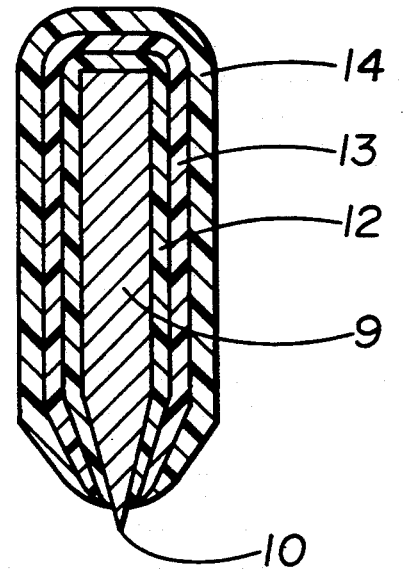
Figure 6:
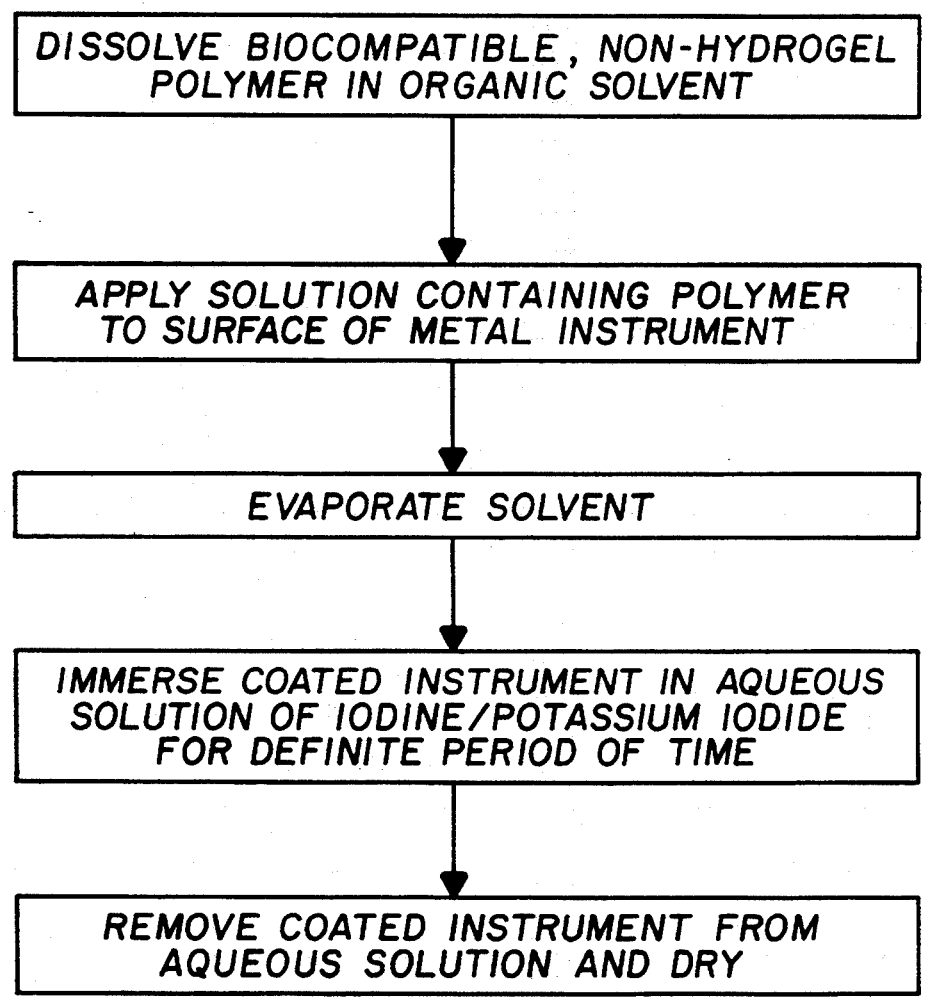
FIG. 6 is a block diagram showing the method of preparing the matrixed coating.
Figure 7:
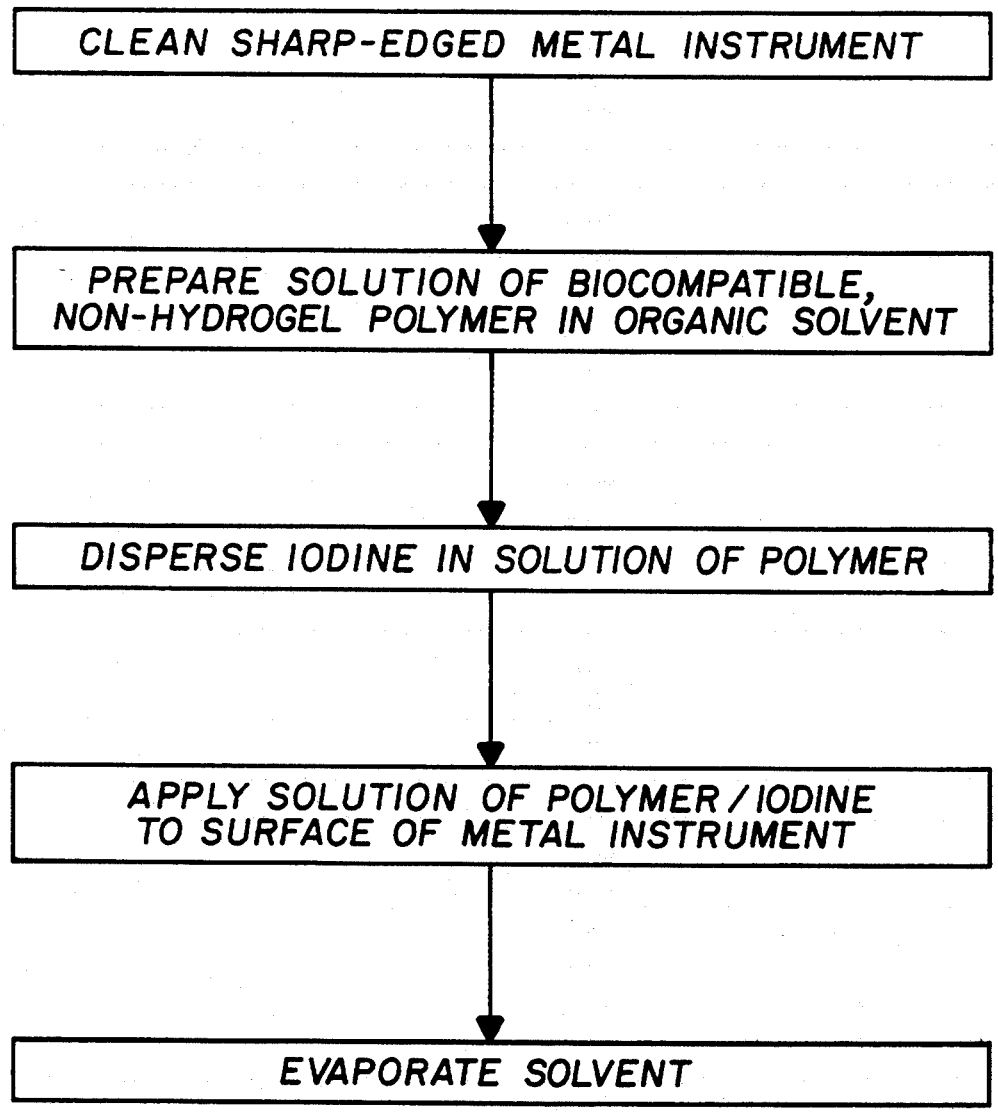
FIG. 7 is a block diagram showing the method of preparing the complexed coating.
Figure 8:
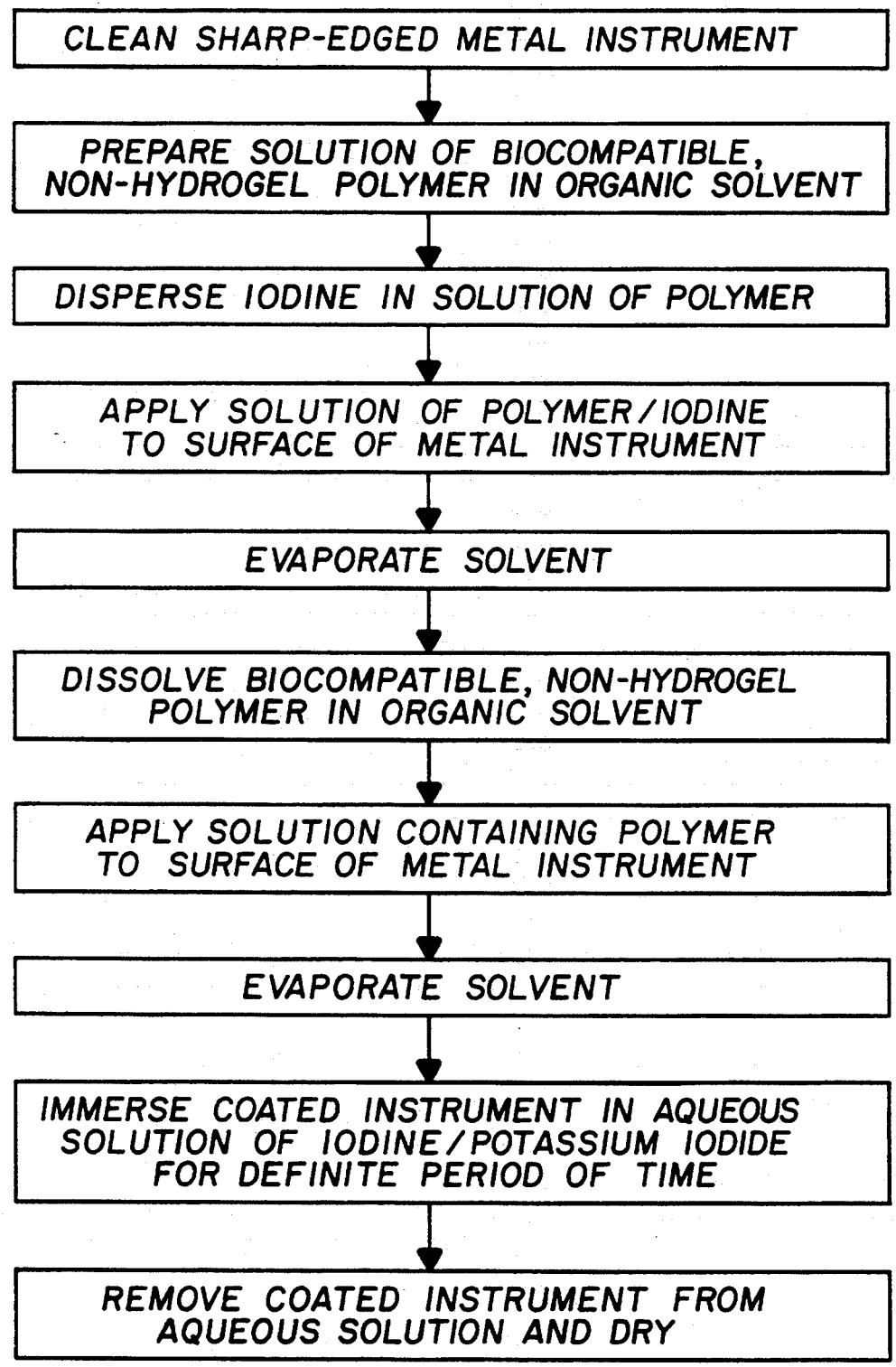
FIG. 8 is a block diagram showing the method of preparing the complexed coating over a matrixed coating.
Figure 9:
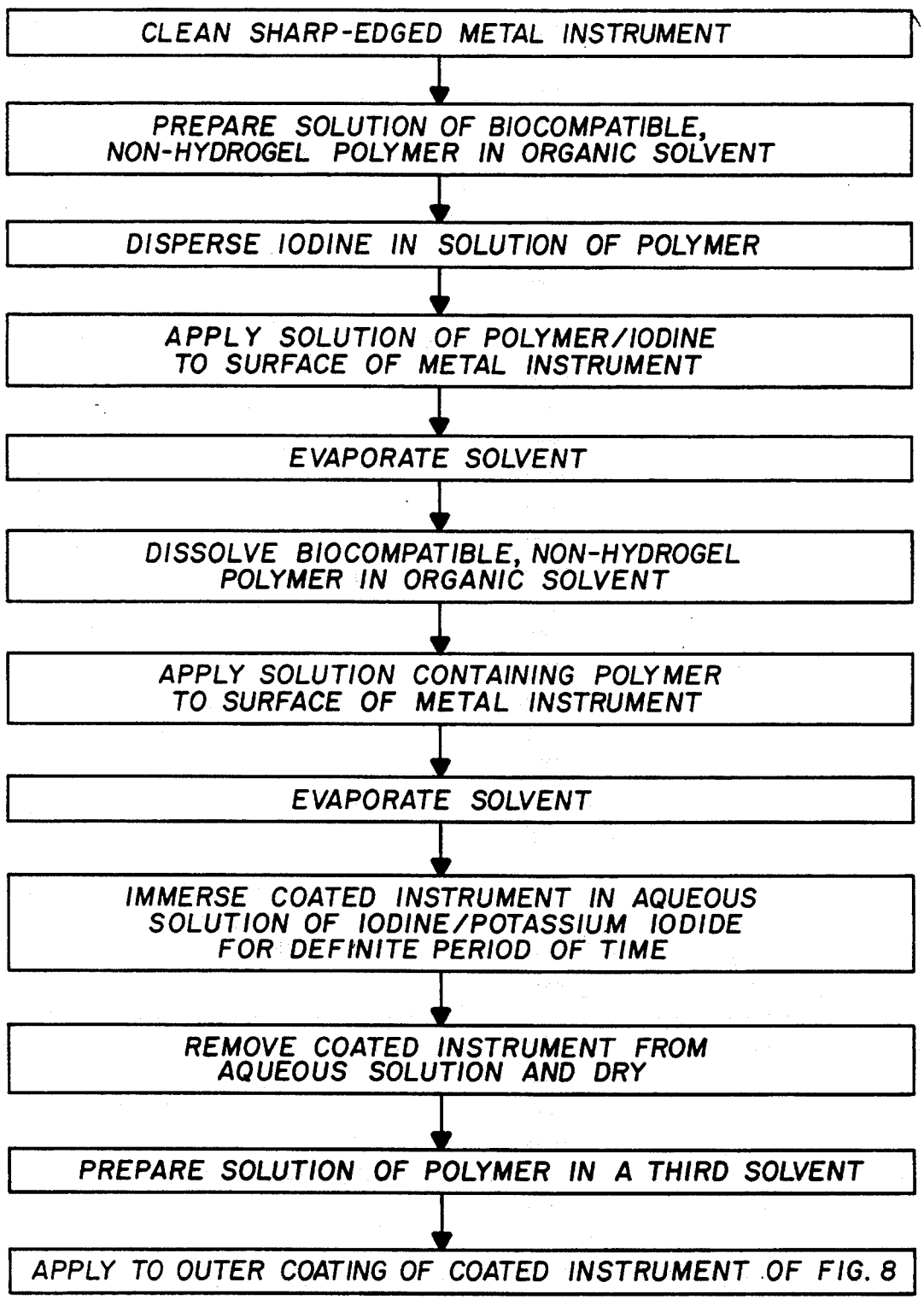
FIG. 9 is a block diagram showing the method of applying a coating without iodine to the coating of FIG. 8.

Referring to FIGS. 5A and 5B, if desired, any of the three aforementioned embodiments of the needles 5 or the cutting blades 9 of the scalpels 8 of the present invention may further include a non-iodized polymer coating 14 that is disposed, respectively, on either the coating 13 or on the coating 12. FIGS. 5A and 5B show the coatings enlarged and not to scale to more clearly show the structure. Further, the inner coating 12 has not been designated as either a complex coating 12' or a matrix coating 12", but either may be used as desired. Provision of this non-iodized polymer coating 14 acts to further shield the iodized coatings 12 and/or 13 from the water in the patient's natural bodily fluids (which contact and dissolve the iodine). In this fashion, the release of the iodine from the coatings 12 and/or 13 may be still further programmed in order to provide a more precise and sustained release of the iodine. The coating is stable at shelf conditions and will not start releasing iodine until it is in contact with body fluids or other fluids. The coated devices were placed in polyethylene bags and stored at room temperature and at 4° C. The devices were tested visually for changes in the coating and in the physical properties of the devices. The iodine content and release were determined in 0.05N KI solution. The devices tested after 6 months at both temperatures, did not show a significant difference from the devices at time zero.

It is noted herein that while the coatings 12, 13 and 14 discussed above are disposed on the exterior surfaces of the cutting blade 9, it is preferred that the coatings 12, 13, 14 are not disposed on the actual tip of the needle 5 or the cutting surface itself. Rather, they are disposed on the needle 5 and in the cutting blade 9 up to the actual cutting surface. This is because such a coating may unacceptably dull the piercing point or cutting edge. In this regard, the coatings 12, 13 and 14 preferably are not to be disposed closer than 1–2 mm relative to the cutting surface. Such placement will still insure that the coatings 12, 13 and 14 are contacted by the bodily fluids during use thereof without interfering with the piercing/cutting action thereof, and the iodine released from the coated surfaces will diffuse to the sharp cutting surfaces and decontaminate them.

As has been mentioned above, in the needles 5 and the cutting blades 9 of the scalpels 8 of the present invention, programmability of iodine released from the coatings 12 and 13 is provided by controlling the release of the iodine from the polymeric complex or matrix. In this regard, it is noted that release is a function of, and varies according to, the thickness, concentration, chemical composition and solubility of the polymer from which the coating 12 or 13 is fabricated. Thus, variation of any or all of these factors may be resorted to in order to program the release of the iodine therefrom.

The variation of the polymer coating thickness alters the release of iodine from the polymer-iodine complexes/matrixes, in that the thicker the coatings, the slower and more sustained will be the release of the iodine from the iodine-polymer complexes and matrixes. This is achieved by the fact that thicker coatings make the contact between the iodine and the water in bodily fluids more difficult to achieve. Control of the thickness of the coating can be achieved by subsequent dippings, dipping the device in polymer having higher concentrations of iodine or by spraying/brushing a thicker coating of the polymer-iodine solution on the surface. The initial release rate is approximately constant irrespective of the thickness of the coating. The non-iodized coating 14 may also be viewed as a rate limiting coating. The thicker the rate limiting coating 14, the slower is the release rate of iodine and the delay time increases as the thickness of the rate limiting coating 14 increases.

The variation of the concentration (or loading) of iodine in the polymer-iodine complexes 13, 12' and matrixes 12" alters the release of iodine from the polymer-iodine complexes/matrixes 13, 12' and 12", respectively, in that the higher the loading of iodine, the more immediate and more sustained will be the release of the iodine from the polymer-iodine complexes 13, 12' and matrixes 12". In this regard, iodine loading varies from 0.01% mg iodine/mg polymer (wt/wt) to 40% mg iodine/mg polymer (wt/wt). The preferred loading value is approximately 0.1% to 25%. To obtain these loading values, the iodine-polymer coating solution is more concentrated with respect to iodine to compensate for evaporation of iodine during the coating process.

The composition of the polymer-iodine coatings 12 and 13 may alter the release of iodine from the polymer-iodine matrixes/complexes 12" and 13, 12', respectively, by altering the release profile of the iodine therefrom. In this respect, the coatings 12, 13 and 14 may further contain various additives, such as inorganic or organic salts, complexing molecules, such as pyrrolidone derivatives, and natural and synthetic oils. For example, to increase the iodine release rate, a fine powder of potassium iodide (KI) or sodium chloride (NaCl) is added to the polymer-iodine coating solution prior to coating of the needle or blade by dipping or spraying. To retain the iodine in the coating and slow the iodine release rate, oligomers and polymers such as vinylpyrrolidone, urea and cellulose may be incorporated in the polymer-iodine complexes and matrixes. In this respect, incorporation of such additives aids in making the release of the iodine from the polymer-iodines complexes/matrixes programmable. A hydrophilic additive, such as polyethylene glycol, increases the release rate since it increases the water penetration into the polymer coating and subsequently increases the leach out of the iodine. In particular, addition of 10% of a polyethylene glycol (PEG 600) decreases the t ½ of an ethyl vinyl acetate coating from 36 hours to 26 hours. If, for example, polyvinylpyrrolidone-iodine complex is used, the release rate will decrease because iodine is complexed and is not free to be released by simple diffusion. In addition to elementary iodine, the polymer may contain anti-inflammatory agents such as steroids and non-steroidal anti-inflammatory agents, such as ibuprofen, naproxen and indomethacin, or antibiotics, such as aminoglycosides, penicillins, cephalosporins, polymyxin, ofloxacillins or anti-fungals such as mycostatin, griseofulvin and ketoconazole. It also may contain anti-thrombogenic drugs such as heparin, prostaglandins and warfarin.

The needles 5 of the syringes and the cutting blades 9 of the scalpels 8 of the present invention will be further understood by reference to the following examples and FIGS. 6–9 which are meant to be illustrative, but not limitative, thereof:

EXAMPLE 1

Polyurethane Coating With Iodine Matrixed Therein

An iodine matrixed polyurethane coating is prepared by dissolving 0.5 grams of iodine crystals in a tetrahydrofuran solution containing 1.5 grams of segmented polyurethane (Estane, TM, Goodrich, Cleveland, Ohio).

Coating is achieved by dipping the needle or cutting blade in the polyurethane-iodine matrix solution. After solvent evaporation, the resulting dark uniform coating of about 0.2 mm may be further coated with a noniodized Ethylene Vinyl Acetate (EVAc) coating by further dipping the polymer-iodine matrix coated needle or cutting blade in a chloroform solution of EVAc. The resultant EVAc coating of 0.05 mm aids in preventing iodine release from the polymer-iodine matrix coating by sublimation.

EXAMPLE 2

A solution of ethylcellulose (3% in ethanol) containing 0.05% iodine was sprayed on a brass surface, a thin uniform coating was obtained which released active iodine when placed in a 0.05% KI solution. The total amount of polymer-iodine that was deposited on the surface was 20 mg/cm$^2$ containing about 0.1 mg iodine which was released constantly for 40 hours when placed in a 0.05N KI solution. Similarly, stainless steel and aluminum surfaces were coated with the same polymeric spray.

EXAMPLE 3

Polyurethane Coating With Iodine Complexed Therein

The needle or cutting blade is first coated with noniodine loaded polyurethane by the dipping thereof in a tetrahydrofuran solution containing 1.5 grams of segmented polyurethane (Estane, TM, Goodrich, Cleveland, Ohio).

Iodine is then complexed into the polyurethane coating by immersing the coated needle or cutting blade in a 20% iodine/potassium iodide ($I_2$/KI) solution in water. The impregnated polyurethane-iodine complex coating is then dried in room air.

The resulting polyurethane-iodine complex coating may then be further coated with a noniodized Ethylene Vinyl Acetate (EVAc) by dipping the coated needle or cutting blade in a chloroform solution of EVAc. The EVAc coating of 0.05 mm prevents iodine release from the polyurethane-iodine complex polymer coating by sublimation.

EXAMPLE 4

Hypodermic needles (20 G, 1.5 inch) were cleaned with acetone and dipped into a 2.5% solution of polymer containing 20% iodine based on the polymer mass. Polyurethane (PU) (Estane), Ethyl Vinyl Acetate (EVAc), and ethylcellulose were used as the polymer coating in tetrahydrofuran (THF), dichloromethane, and ethanol solutions, respectively. A uniform coating that strongly adhered to the metal surface was obtained with the three polymers. The coated needles were further treated by immersing them in a 5% iodine/potassium iodide water solution for additional iodine loading by complexation. The EVAc coated needle was further coated with a PU iodine free coating by dipping the needle into a 1% PU in THF. The in vitro release of iodine in a potassium iodide solution was determined at 37° C. and the time for 50% iodine release is given. The total mass increase and iodine content was as follows:

| Coating | Coating mass | Iodine loading | Release time (t ½) |
| --- | --- | --- | --- |
| ethylcellulose | 6.3 mg | 0.3 mg | 20 h |
| EVAc | 4.5 | 0.7 mg | 40 h |
| PU | 5.2 | 0.6 mg | 45 h |
| PU + Complex | 5.8 | 0.75 mg | 24 h |
| EVAc + coating | 5.3 | 0.7 mg | 62 h |

The needles were loaded with a significant amount of iodine and 50% of the loaded iodine was released within the first two days in vitro. The PU matrix +complexed iodine coating rapidly released the complexed iodine, thus the t ½ was decreased. The EVAc double coated needle had a longer t ½ because of the second coating which reduces the drug release rate from the coated surface.

The uniodized polyurethane coating absorbed an additional 0.15 mg iodine (about 25%) while the other polymers absorbed negligible amounts of complexed iodine. This experiment demonstrates the utilization of programmable iodine releasing system for metal surfaces.

The rate of release from a coated surface was further shown to be controllable by depositing the polymer/iodine coating on culture cluster plates.

EXAMPLE 5

Having demonstrated that the needles and blades can be effectively coated with a polymer that is programmed to release iodine for periods that are long enough and at concentrations that are high enough to theoretically inactivate the HIV virus, the next experiment consists of effectively proving that the programmable-iodine releasing polymer is able to inactivate the virus. Due to laboratory regulations that, for safety reasons, prevent lab personnel from working with sharp instruments that are contaminated with HIV, the programmable iodine-loaded polymer had to be tested using culture plates that are usually used in viral cultures.

Polyurethane-iodine complex: 24 well culture cluster plates (Costar, Cambridge Mass.) were coated with polyurethane by spreading 50 microliters of polyurethane (PU) solution in tetrahydrofuran (THF, 2.5 weight %) per well. After solvent evaporation, a uniform thin coating of 0.4 mg/cm² was obtained. To each well 3 ml iodine-potassium iodide solutions were added and allowed to react for 60 minutes at room temperature. The solutions were discarded and the wells were rinsed with deionized water for 10 minutes and left to dry at room air for 24 hours. The iodine concentrations in the solution were 1.0M, 0.1M, 0.05M, 0.01M, and 0.001M; the potassium iodide concentrations were 1.5 times the molarity of iodine in the solutions. For each concentration a total of four (4) wells were used. The total amount of iodine absorbed in the PU-iodine complex was 4, 1, and 0.5 weight % (50, 12 and 5 microgram per well), based on the polyurethane coating, from 1, 0.1, and 0.05M iodine solution, respectively. The 0.01M and 0.001M solutions did not provide detectable amounts of iodine.

Iodine release was studied by adding into the wells 3 ml phosphate buffer pH 7.4 at 37° C., or in 0.01M potassium iodide solution at 25° C. The solutions were replaced frequently with fresh solutions and the iodine concentrations in the solutions were determined by UV absorption at 280 nm.

Figure 10:
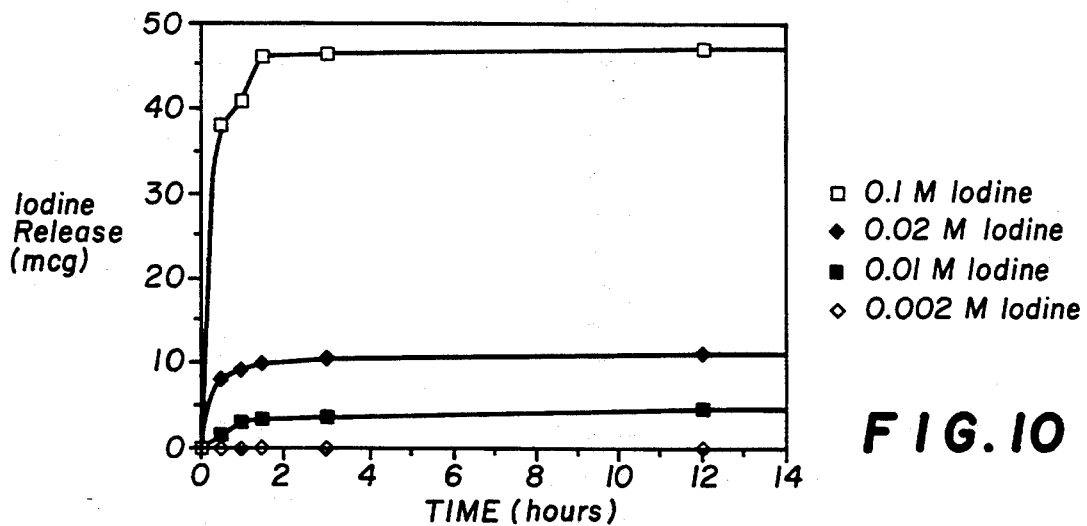
FIG. 10 is a graph of the rate of iodine release from a polymer iodine complex in phosphate buffer.
Figure 11:
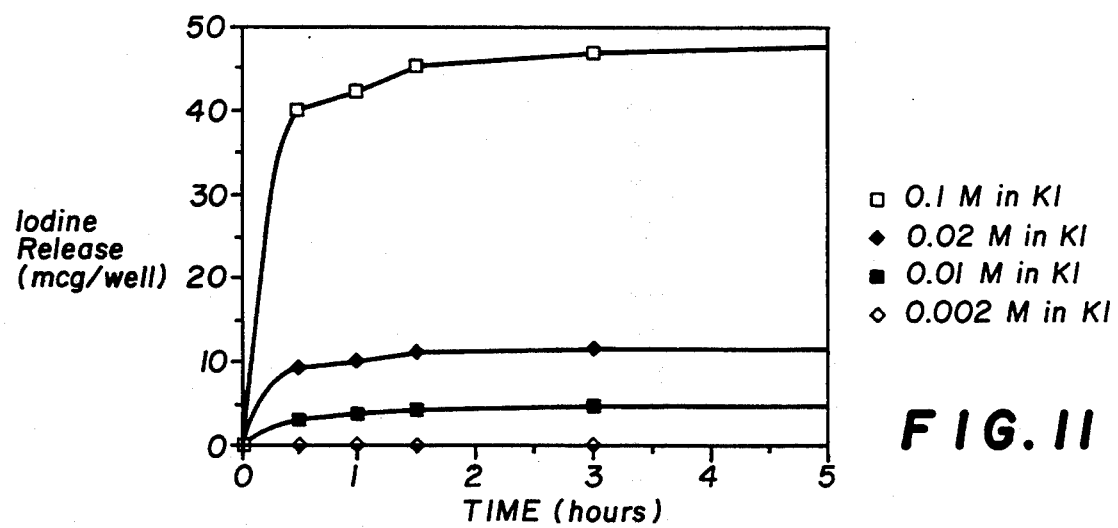
FIG. 11 is a graph of the rate of iodine release from a polymer iodine complex in potassium iodide.

The in-vitro release from polyurethane-iodine complex was rapid both in phosphate buffer and in potassium iodide solution. In phosphate buffer pH 7.4 at 37° C., iodine was released rapidly from the coating with about 90% of the iodine released in 3 hours, the remaining 10% was released constantly in the following 48 hours (FIG. 10). The release in potassium iodide solution was even faster and 90% of the iodine content was released in 1 hour. The increase in iodine release in potassium iodide solution was due to the higher solubility of iodine in potassium iodide solution (FIG. 11).

EXAMPLE 6

Polyurethane-iodine matrix: 24 well plates (Costar) were coated with polyurethane-iodine by spreading 50 microliters of polyurethane-iodine (PU-iodine) solution in tetrahydrofuran (THF, 2.5 weight %) in each well. After solvent evaporation a dark coating was obtained. The iodine concentration in the polyurethane coating was 10, 20, and 30% based on the polyurethane. The total iodine content in the PU-iodine matrices was 120, 240 and 360 micrograms of iodine per well for the 10, 20 and 30 weight % PU-iodine coating. For each concentration, four wells were used.

Figure 12:
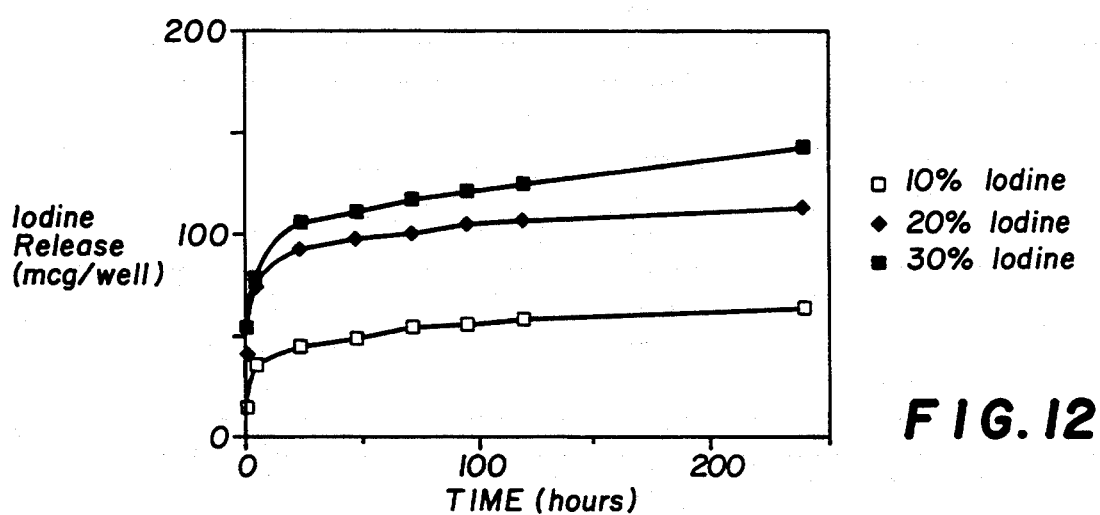
FIG. 12 is a graph of the rate of iodine release from a polymer iodine matrix in potassium iodide.

The release of iodine from the polyurethane-iodine matrix in phosphate buffer was very slow and was dependent on the solution in which the polymer is placed. In phosphate buffer solution, a negligible amount of iodine was released in 3 days. On the other hand, in potassium iodide solution, a significant amount of iodine was released for 10 days. About 70 to 80% of the iodine was released in 24 hours, and the rest was released constantly over a period of more than 10 days (FIG. 12).

By changing the thickness of the polymer coating and by using more than one polymer coating (e.g. using a combination of polyurethane-iodine matrix or polyurethane-iodine complexes, with a second coating of polyurethane-iodine complex or uniodized polymer), the amount and duration of iodine release can be programmed at the time of the coating. Using this approach, the duration of iodine release can be sustained for up to several months.

The effectiveness of the polyurethane-iodine coating has been demonstrated with HIV virus grown in tissue culture plates that have been coated with the coating of the present invention.

The in-vitro anti-HIV activity of the polyurethane-iodine coated plates was assessed by incubating HIV −3B virus in coated plates for 15 minutes, 30 minutes, 90 minutes, 3 hours, 6 hours, 12 hours and 24 hours prior to infection of the human lymphocyte (MT4) cells (5×100,000 cells/ml) at a multiplicity of infection of 100×tissue culture infections dose (TCID) 50. The plates were coated with polymers that release different concentrations of iodine (1.8, 5.8, 7.3, and 9.2 μg of iodine/ml). The virus, and thus the coated plates, were diluted 1:20 before adding the cells. The infection was allowed to incubate at 37° C. for one hour, at which time the cells were diluted with culture medium RPM1 1640 supplemented with 10% heat-inactivated fetal bovine serum and 10% interleukin-2 to a cell density of 8×10,000 cells/ml. The cells were then seeded onto 96-well plates and incubated at 37° C. Five days later, the cell-free supernatant was analyzed for reverse transcriptase and cells infected with virus exposed to plates coated with the present invention for 24 hours were analyzed for cell growth.

The MT4 cells that were exposed to the polyurethane-iodine complex multiplied as rapidly as control non-infected cells, indicating complete inactivation of the HIV. As expected, the polyurethane-iodine matrices did not show any activity against the virus, due to the slow release of iodine into the culture medium over the time period of the experiment.

Figure 13:
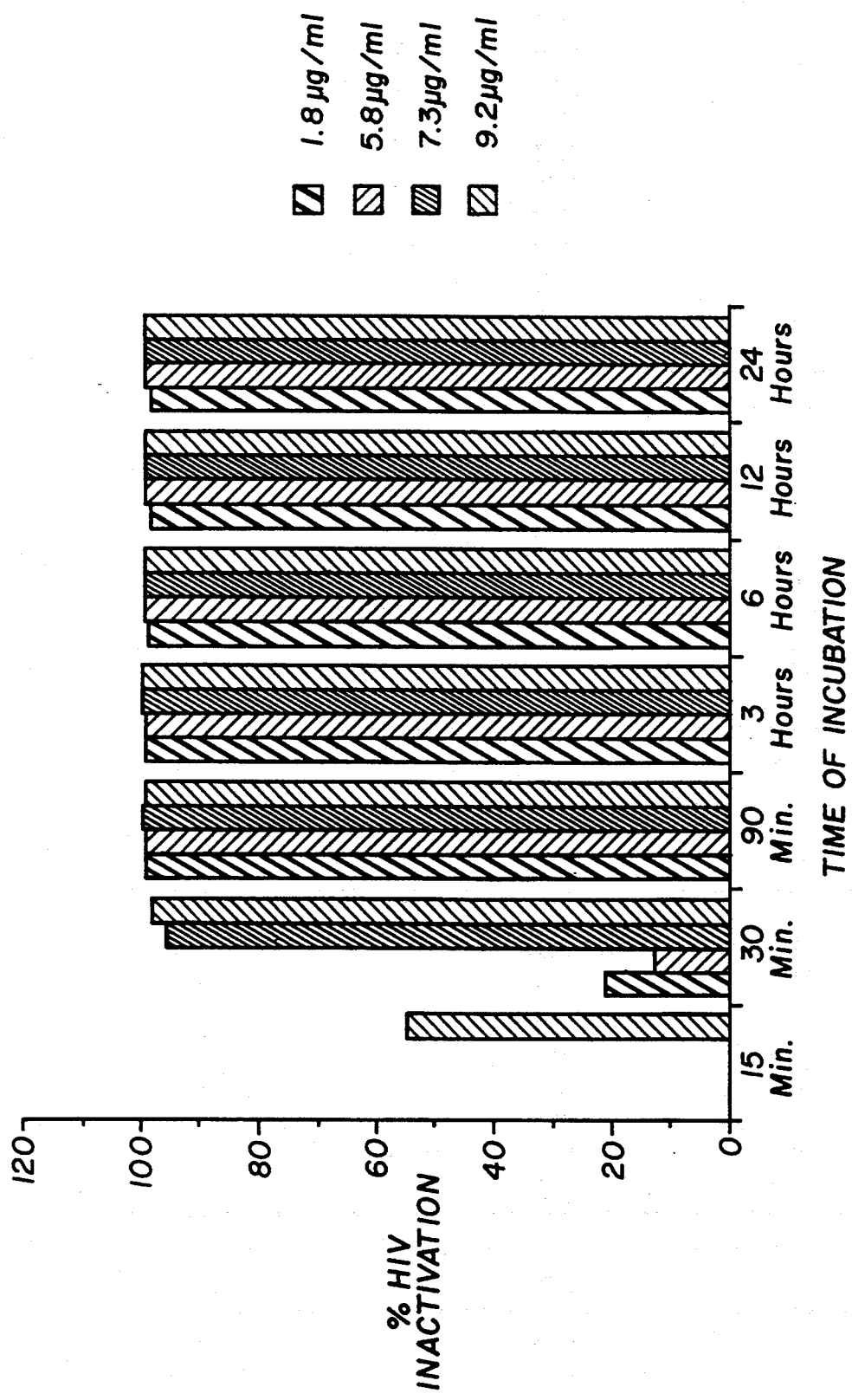
FIG. 13 is a bar chart of the inactivation of HIV virus by the coating of the present invention.

A quantitative analysis of the HIV inactivation was done in the polyurethane-iodine complex plates, by analyzing the cell-free supernatant for reverse transcriptase (RT). The data are tabulated in Table I below and summarized in FIG. 13.

Table I indicates that while only partial inactivation of HIV 3B was achieved after 15 minutes incubation in plate number 4, full inactivation of the virus was observed after only 30 minutes incubation in both plates 3 and 4. Complete inactivation of the virus was achieved in all plates after 90 minutes incubation and continued through 24 hours incubation. Interestingly, the cells exposed to virus incubated in the plates for 24 hours grew as rapidly as uninfected cells, indicating that the iodine released in the media did not affect the growth of the MT4 cells themselves.

TABLE I

Analysis of HIV Inactivation by Reverse Transcriptase (RT) assay

|  | cpm (average of 3 wells) | % Inhibition of HIV |
|---|---|---|
| 15 minute incubation Plate | | |
| Control | 215350 | — |
| 1.8 μg Iodine/ml | 225358 | 0 |
| 5.8 μg Iodine/ml | 234782 | 0 |
| 7.3 μg Iodine/ml | — | — |
| 9.2 μg Iodine/ml | 96907 | 55 |
| 30 minute incubation Plate | | |
| Control | 229862 | — |
| 1.8 μg Iodine/ml | 183397 | 21 |
| 5.8 μg Iodine/ml | 201128 | 13 |
| 7.3 μg Iodine/ml | 13219 | 96 |
| 9.2 μg Iodine/ml | 4931 | 98 |
| 90 minute incubation Plate | | |
| Control | 285898 | — |
| 1.8 μg Iodine/ml | 1489 | 99.5 |
| 5.8 μg Iodine/ml | 950 | 99.7 |
| 7.3 μg Iodine/ml | 648 | 99.8 |
| 9.2 μg Iodine/ml | 923 | 99.7 |
| 3 hour incubation Plate | | |
| Control | 259064 | — |
| 1.8 μg Iodine/ml | 948 | 99.7 |
| 5.8 μg Iodine/ml | 739 | 99.7 |
| 7.3 μg Iodine/ml | 512 | 99.8 |
| 9.2 μg Iodine/ml | 622 | 99.8 |
| 6 hour incubation Plate | | |
| Control | 147961 | — |
| 1.8 μg Iodine/ml | 1731 | 99 |
| 5.8 μg Iodine/ml | 917 | 99.4 |
| 7.3 μg Iodine/ml | 621 | 99.6 |
| 9.2 μg Iodine/ml | 460 | 99.7 |
| 12 hour incubation Plate | | |
| Control | 147961 | — |
| 1.8 μg Iodine/ml | 1731 | 99 |
| 5.8 μg Iodine/ml | 917 | 99.4 |
| 7.3 μg Iodine/ml | 621 | 99.6 |
| 9.2 μg Iodine/ml | 460 | 99.7 |
| 24 hour incubation Plate | | |
| Control | 131116 | — |
| 1.8 μg Iodine/ml | 1970 | 98.5 |
| 5.8 μg Iodine/ml | 859 | 99.4 |
| 7.3 μg Iodine/ml | 636 | 99.5 |
| 9.2 μg Iodine/ml | 552 | 99.6 |
| Mock-Infected Plate | cpm | |
| Control | 559 | |
| 1.8 μg Iodine/ml | 565 | |
| 5.8 μg Iodine/ml | 503 | |
| 7.3 μg Iodine/ml | 531 | |
| 9.2 μg Iodine/ml | 501 | |

The above experiment effectively demonstrated that the programmable iodine releasing polymer that is coated on culture plates can inactivate the HIV virus. The next experiment proves that the same polymer coating can be successfully applied to the metal surfaces of needles and scalpel blades and that it can release concentrations of iodine that are of the same magnitude or even higher than those needed to inactivate the HIV virus. Hypodermic needles and scalpel blades (three for each experiment) were coated with polyurethane-iodine complexes as follows: Needles (G18, 1.5 inches long) and scalpels (15 blades) were dipped for 10 seconds in a 2.5 weight % polyurethane (Estan) solution and then immersed in an aqueous iodine solution (0.1M in 0.15M KI water solution) for about 5 minutes, washed with deionized water and let to dry at room air to form a thin uniform browning coat. The thin brown coated devices were placed in 0.01 N KI solution and the iodine release was monitored as a function of time. The results are given as the cumulative release from a needle or scalpel. The amount released from the needles and scalpels over time are:

| Time (min): | 15 | 30 | 45 | 60 | 120 | 240 | 5 hr | 24 hr |
|---|---|---|---|---|---|---|---|---|
| Needle (μg/needle): | 4.1 | 5.3 | 6.2 | 6.6 | 7.2 | 7.1 | 7.5 | 7.8 |
| Scalpel (μg/scalpel): | 2.6 | 4.2 | 4.5 | 4.6 | 4.7 | 4.7 | 4.8 | 4.9 |

For comparison, as shown in Table I, the % inactivation of the HIV virus and the culture plate at the different levels of iodine was:

| Time (min): | 15 | 30 | 90 | 180 | 6 hr | 12 hr | 24 hr |
|---|---|---|---|---|---|---|---|
| 1.8 μg Iodine/ml | — | 21 | 99.5 | 99.7 | 99 | 99 | 98.5 |
| 5.8 μg Iodine/ml | — | 13 | 99.7 | 99.7 | 99.7 | 99.4 | 99.4 |
| 7.3 μg Iodine/ml | — | 96 | 99.8 | 99.8 | 99.6 | 99.6 | 99.5 |
| 9.2 μg Iodine/ml | 55 | 98 | 99.7 | 99.8 | 99.7 | 99.7 | 99.6 |

Thus, it is evident that the amount of iodine released from the coated needles and scalpels is significant and is more than sufficient to inactivate the HIV virus.

The polymer-iodine coating is also effective when used with hepatitis B virus (HBV), other viruses, bacteria, fungi, mycobacteria and spores. Iodine is a universal anti-infective agent with no known microbial resistance.

What is claimed is:

1. A sharp-edged metal instrument coated with an anti-infective coating comprising said instrument coated with an anti-infective coating which is insoluble in a biological medium and which is able to be bound to said sharp-edged metal instrument during storage, use and initial disposal thereof, the anti-infective coating including a biocompatible, non-hydrogel polymer, said polymer being compatible with and binding to the sharp-edged metal instrument, said polymer being soluble in an organic solvent, and iodine complexed with the polymer coating for programmed rapid release of the iodine from the polymer coating when the sharp-edged instrument penetrates the skin of the patient and contacts blood or other body fluids.

2. The anti-infective coating of claim 1, wherein the polymer is selected from the group consisting of polyurethane and polyurea.

3. The anti-infective coating of claim 1, wherein the solvent is selected from the group consisting of alcohols, ketones, ethers, halogenated aliphatic hydrocarbons and aromatic hydrocarbons.

4. The anti-infective coating of claim 1, wherein the iodine loading is approximately 0.01% to 40% iodine.

5. The anti-infective coating of claim 1, wherein the coating has a thickness, the thickness being approximately 0.1 to 0.22 mm.

6. The anti-infective coating of claim 1, wherein the sharp-edged instrument is a needle having a cannula.

7. The anti-infective coating of claim 1, wherein the sharp-edged instrument is a scalpel.

8. A method of preparing a programmed, rapid release anti-infective coating for a metal instrument having a sharp edge, the coating releasing iodine for a period of time at a concentration sufficient to inhibit human immunodeficiency virus, hepatitis B virus and other germs, said sharp-edged metal instrument used to penetrate a skin of a patient, the anti-infective coating being insoluble in a biological medium and being bound to the sharp-edged metal instrument, the method comprising the steps of:

dissolving a biocompatible, non-hydrogel polymer in an organic solvent, applying the solution containing said polymer to the sharp-edged metal instrument, evaporating the solvent to form a uniform polymer coating on the sharp-edged metal instrument, immersing the coated sharp-edged metal instrument into a solution of iodine and potassium iodide in water for approximately 0.03 to 60 minutes, and drying the iodine complexed polymer coated sharp-edged metal instrument.

9. A sharp-edged metal instrument coated with an anti-infective coating comprising said instrument coated with an anti-infective coating being insoluble in a biological medium and being bound to the sharp-edged metal instrument, the anti-infective coating including a biocompatible, non-hydrogel polymer, said polymer being compatible with and binding to a surface of the sharp-edged metal instrument, said polymer being soluble in an organic solvent, and having iodine matrixed with the coating for programmed sustained release of the iodine from the coating when the sharp-edged instrument penetrates the skin of the patient.

10. The anti-infective coating of claim 9, wherein the polymer is selected from the group consisting of polyurethane, ethylene vinyl acetate, polyvinyl chloride, polyesters, nylon, polyacrylamide, polycarbonate, polyethylene, polymethyl methacrylate, cellulose esters (like ethyl, methyl, propyl and hydroxypropyl), propylene, polystyrene, polytetrefluoroethylene, polyvinylchloride, poly(ethylvinyl acetate), elastomeric organosilicon polymers, poly(hydroxy alkyl esters) and combinations thereof.

11. The anti-infective coating of claim 9, wherein the solvent is selected from the group consisting of alcohols, ketones, ethers, halogenated aliphatic hydrocarbons and aromatic hydrocarbons.

12. The anti-infective coating of claim 9, wherein the iodine loading is approximately 0.01% to 40% iodine.

13. The anti-infective coating of claim 9, wherein the coating has a thickness, the thickness being approximately 0.1 to 0.22 mm.

14. The anti-infective coating of claim 9, wherein the sharp-edged instrument is a needle having a cannula.

15. The anti-infective coating of claim 9, wherein the sharp-edged instrument is a scalpel.

16. The anti-infective coating of claim 9, wherein at least 2.6 micrograms of iodine are released from the coated instrument, the released iodine inactivating at least 99% of a human immunodeficiency virus.

17. A method of preparing a programmed sustained release anti-infective coating for a metal instrument having a sharp-edge, the coating releasing iodine for a period of time at a concentration sufficient to inhibit human immunodeficient virus, hepatitis B virus and other germs, said sharp-edged metal instrument used to penetrate the skin of a patient, the anti-infective coating being insoluble in a biological medium and being bound to the sharp-edged metal instrument, the method comprising the steps of:

cleaning the sharp-edged metal instrument,
preparing a solution of a biocompatible, non-hydrogel polymer in an organic solvent,
dispersing iodine in the solution of the polymer,
applying the polymer/iodine solution to the sharp-edged metal instrument,
evaporating the solvent to form a uniform polymer/iodine coating on the sharp-edged metal instrument.

18. The method of claim 17, wherein at least 2.6 micrograms of iodine are released from the coated instrument, the released iodine inactivating at least 99% of a human immunodeficiency virus.

19. In combination with a medical device having a metallic "sharps" portion intended to pierce a human body having body fluids, a substantially biocompatible, anti-microbial, anti-viral coating on the metallic "sharps" portion, the coating being fully compatible with the normal use of the medical device and comprising a non-hydrogel polymer having dispersed therein a solid solution of iodine, wherein the iodine has a programmable timed release when exposed to the body fluids, and wherein the coating remains substantially on the device during storage, use and initial disposal thereof.

20. The combination of claim 19, wherein the coating releases at least 2.6 micrograms of iodine and inactivates at least 99% of a human immunodeficiency virus.

21. The combination of claim 19, wherein the coating comprises a first inner coating in which the iodine is matrixed, and a second outer coating in which the iodine is complexed, thereby providing long-term and short-term programmable timed release of the iodine, respectively.

22. The combination of claim 21, wherein the second outer coating further is coated with a biocompatible third coating, the third coating having no iodine therein, the third coating providing a timed programmed release of the iodine from the first coating and the second coating.

23. A method of preparing a programmed release anti-infective multiple coating for a metal instrument having a sharp-edge, the coating releasing iodine for a period of time at a concentration sufficient to inhibit human immunodeficiency virus, hepatitis B virus and other germs, said sharp-edged metal instrument used to penetrate the skin of a patient, the anti-infective coating being insoluble in a biological medium and being bound to the sharp-edged metal instrument, the method comprising the steps of:
cleaning the sharp-edged metal instrument,
preparing a solution of a first biocompatible, non-hydrogel polymer in a first organic solvent,
dispersing iodine in the solution of the polymer,
applying the polymer/iodine solution to the sharp-edged metal instrument,
evaporating the first organic solvent to form a uniform first polymer/iodine coating on the sharp-edged metal instrument,
dissolving a second biocompatible, non-hydrogel polymer in a second organic solvent to form a second solution, applying the second solution containing said polymer to the first polymer/iodine coating on the sharp-edged metal instrument, evaporating the second solvent to form a second uniform polymer coating on the sharp-edged metal instrument, immersing the coated sharp-edged metal instrument into a solution of iodine and potassium iodide in water for approximately 0.03 to 60 minutes, and drying the iodine complexed polymer coated sharp-edged metal instrument,
wherein the outer coating provides short term programmable timed release of iodine and the inner coating provides long term programmable release of iodine.

24. The method of inhibiting H.I.V., hepatitis B and other viruses and germs when using an instrument during a medical procedure on a patient, comprising the steps of providing a sharp instrument, coating the sharp instrument with an anti-infective coating of a polymer having iodine therein, inserting the coated sharp instrument through the patient's skin, such that the coating on the sharp instrument contacts a fluid in the patient's body to thereby release iodine from the coating, removing the instrument from the patient, and disposing of the instrument.

25. The method of claim 24, wherein the coating comprises a first coating, and wherein the iodine is complexed in the first coating for a rapid release of the iodine over a relatively-short time interval.

26. The method of claim 25, further including a second coating between the first coating and the instrument, and wherein the iodine is matrixed in the second coating for a sustained release of the iodine over a relatively-long time interval.

27. The method of claim 24, wherein the coating is insoluble in a biological medium such that the coating remains on the sharp instrument when in contact with the body fluid.

28. The method of claim 24, wherein the instrument comprises a needle.

29. The method of clam 24, wherein the instrument comprises a scalpel.

30. The method of inhibiting H.I.V., hepatitis B and other viruses and germs when using a needle during a medical procedure on a patient, comprising the steps of providing the needle, coating the needle with an anti-infective coating of a polymer having iodine therein, the coating being insoluble in a biological medium and including a first coating having the iodine complexed therein for a rapid release of the iodine over a relatively-short time interval, and further including a second coating between the first coating and the needle and having the iodine matrixed therein for a sustained release of the iodine over a relatively-long time interval, inserting the needle through the patient's skin such that the coating on the needle contacts a fluid in the patient's body to thereby release the iodine from the coating, removing the instrument from the patient, and disposing of the instrument.

31. The method of inhibiting H.I.V., hepatitis B and other viruses and germs when using a scalpel during a medical procedure on a patient, comprising the steps of providing the scalpel including a blade having a sharp edge, coating the sharp edge of the blade with an anti-infective coating of a polymer having iodine therein, the coating being insoluble in a biological medium and including a first coating having the iodine complexed therein for a rapid release of the iodine over a relatively-short time interval, and further including a second coating between the first coating and the sharp edge of the blade and having the iodine matrixed therein for a sustained release of the iodine over a relatively-long time interval, using the coated sharp edge of the blade to make an incision on the patient, such that the coating on the sharp edge of the blade contacts a fluid in the patient's body to thereby release iodine from the coating, removing the scalpel from the incision in the patient, and disposing of the blade.

32. A method of using a sharp-edged metal instrument having an anti-infective coating thereon, the coating releasing iodine for a period of time at a concentration sufficient to inhibit human immunodeficiency virus, hepatitis B virus and other germs, said sharp edged metal instrument piercing the skin of a patient's body having body fluids, the anti-infective coating being insoluble in a biological medium and being bound to the sharp-edged metal instrument, the method comprising the steps of: inserting the sharp-edged metal instrument into the patient's body to penetrate the skin and to contact the body fluids, wherein release of iodine is initiated; removing the sharp-edged metal instrument from the living body; disposing of the sharp-edged metal instrument wherein release of iodine continues over a programmed period of time to inhibit the germs and reduce the possibility of subsequent infection.

* * * * *